United States Patent [19]
Hines et al.

[11] Patent Number: 5,959,300
[45] Date of Patent: *Sep. 28, 1999

[54] ATTENUATION CORRECTION IN A MEDICAL IMAGING SYSTEM USING COMPUTED PATH LENGTHS AND ATTENUATION VALUES OF A MODEL ATTENUATION MEDIUM

[75] Inventors: Horace H. Hines, San Jose; William K. Braymer, Pleasanton; John R. Liebig, San Jose, all of Calif.

[73] Assignee: ADAC Laboratories, Milpitas, Calif.

[*] Notice: This patent is subject to a terminal disclaimer.

[21] Appl. No.: 08/833,684

[22] Filed: Apr. 8, 1997

Related U.S. Application Data

[63] Continuation-in-part of application No. 08/580,843, Dec. 29, 1995, Pat. No. 5,682,036.

[51] Int. Cl.$^6$ ................................................. G01T 1/166
[52] U.S. Cl. ............................. 250/363.09; 250/252.1 R
[58] Field of Search ........................ 250/363.09, 363.04, 250/363.07, 252.1 R

[56] References Cited

U.S. PATENT DOCUMENTS

| 5,155,365 | 10/1992 | Cann et al. | 250/363.02 |
| 5,338,936 | 8/1994 | Gullberg et al. | 250/363 |
| 5,376,795 | 12/1994 | Hasegawa et al. | 250/363.04 |
| 5,682,036 | 10/1997 | Hines et al. | 250/363.09 |
| 5,767,517 | 7/1998 | Hawkins | 250/363.04 |
| 5,814,817 | 9/1998 | Guillemaud et al. | 250/363.04 |

OTHER PUBLICATIONS

Tan, Patrick et al., "A Scanning Line Source for Simultaneous Emission and Transmission Measurements in SPECT", *The Journal of Nuclear Medicine*, vol. 34, No. 10, Oct. 1993, pp. 1752–1760.

T.F. Budinger et al., "Three–Dimensional Reconstruction in Nuclear Medicine Emission Imaging," *IEEE Transactions on Nuclear Science*, vol. NS–21, Jun. 1974, pp. 2–20.

Walter William Peppler, "Combined Transmission–Emission Scanning Using Dual–Photon Absorptiometry," thesis in partial fulfillment for the requirements for the degree of Doctor of Philosophy, University of Wisconsin, 1981, *UMI Dissertation Services*, 1998, pp. 1–126.

*Primary Examiner*—Edward P. Westin
*Assistant Examiner*—Richard Hanig
*Attorney, Agent, or Firm*—Blakely, Sokoloff, Taylor & Zafman LLP

[57] ABSTRACT

A method of correcting for attenuation during emission imaging in a gamma camera medical imaging system. Attenuation values are determined empirically and are stored in a look-up table in a memory that is readable by the imaging system, with each attenuation value corresponding to a given thickness value. The attenuation values are computed before imaging is performed by first measuring the number of photons which pass from a transmission source through various known depths of water or another suitable model attenuator, using the same radiation source as will be used for emission imaging. For each depth, the measurement is then used to compute the actual attenuation for a thickness of the model attenuator. The attenuation is then stored as a value in the look-up table with corresponding values of attenuator thickness and is later used to correct emission data for the effects of attenuation.

19 Claims, 12 Drawing Sheets

FIG_3

FIG_4

FIG_5

FIG_6

FIG_7

FIG_8

FIG_9

| x (cm) | I / I$_0$ |
|--------|-----------|
| 0      | 1.0       |
| 5      | V$_1$     |
| 10     | V$_2$     |
| 15     | V$_3$     |
| 20     | V$_4$     |
| .      | .         |
| .      | .         |
| .      | .         |

FIG_10

FIG_11

FIG_12

ATTENUATION CORRECTION IN A MEDICAL IMAGING SYSTEM USING COMPUTED PATH LENGTHS AND ATTENUATION VALUES OF A MODEL ATTENUATION MEDIUM

This application is a continuation-in-part of application Ser. No. 08/580,843, filed on Dec. 29, 1995, now U.S. Pat. No. 5,682,036.

FIELD OF THE INVENTION

The present invention pertains to the field of nuclear medicine.

More particularly, the present invention relates to calibrating a non-uniform attenuation map for emission computed tomography.

BACKGROUND OF THE INVENTION

In emission computed tomography (ECT), images of internal structures of the body are generated by injecting a patient with a radiopharmaceutical and then using a gamma camera to detect emitted gamma rays, or photons, from various angles around the body. Photons reaching a gamma camera's scintillation detectors produce scintillation events, which are detected by photomultiplier tubes and then converted by circuitry into electrical signals representing both position and energy information. These signals are then used to generate image data in a process known as reconstruction.

An effect known as photon attenuation is an important factor which affects the accuracy of images collected using ECT. Photon attenuation tends to degrade images by introducing image artifacts and other distortions that can result in false positive detection of lesions or the failure to detect lesions. Non-uniform photon attenuation creates image degradation by interfering with and partially absorbing the radiation emitted from an organ containing the radiopharmaceutical. Since each patient that is imaged using a gamma camera is different (different shape, different size, etc.), the tissue and bone structure surrounding an organ of interest are different for each patient. This surrounding tissue and bone structure attenuates the radiation emitted from a radiopharmaceutical distributed within the organ. The attenuation of the radiation is non-uniform because the attenuation coefficients of the different tissues and bone are different. Hence, radiation attenuation non-uniformly reduces the count density in the images of views from different angles. This attenuation can lead to falsely identifying an artifact when, in fact, healthy tissue is imaged and vice-versa.

Non-uniform attenuation caused by the body can be compensated for if an "attenuation map" of the body is determined. An attenuation map comprises a number of attenuation coefficient values corresponding to different points within the body. Transmission computed tomography is a technique which allows a gamma camera and a processing computer system to generate a non-uniform attenuation map of an individual patient. Generally, during transmission scanning, radiation from a transmission source having known properties is transmitted through the patient and then detected by a scintillation detector. By knowing the intensity of the radiation transmitted by the source and measuring the intensity of radiation which passes through the object, a computer within the gamma camera system can measure the extent of non-uniform attenuation over different parts of the body at different angles. From this information, a non-uniform attenuation map of the body can be reconstructed using well-known methods and procedures. The non-uniform attenuation map is then used during the emission reconstruction process to correct emission image data collected during ECT imaging.

Transmission scanning and emission scanning are often performed at different energy levels to allow simultaneous acquisition. Consequently, the attenuation map, which is initially based on the transmission energy level, must be calibrated to the emission energy level in order to use the attenuation map to correct emission image data. For example, a transmission scan might be performed at an energy level of 100 keV using Gd-153, while the emission scan is performed using an energy level of 140 keV using Tc-99 m. Calibration of the attenuation map generally involves scaling the coefficients of the attenuation map to correspond to the emission energy level. Calibration is performed by the computer in the gamma camera system executing computer program instructions that define the scaling operation. The use of an accurate scaling factor in calibrating the attenuation map is necessary for generating accurate emission images. However, for various reasons, the determination of an accurate scaling factor for calibration is problematic. One reason such a determination can be difficult is the scattering within the body of photons emitted from an organ of interest.

Therefore, it is desirable to provide for more accurate calibration of an attenuation map for use in correcting emission image data in ECT.

SUMMARY OF THE INVENTION

A method is provided of enabling a medical imaging system to correct emission data for the effects of attenuation that occurs within an object to be imaged, such as a patient. The imaging system includes a processor for processing the emission data. According to the method, a number of attenuation values are experimentally determined using an attenuating medium that is representative of the object to be imaged. Each of the attenuation values corresponds to a given thickness of the attenuating medium. The attenuation values and a number of corresponding thickness values are then stored in a storage medium that can be read by the processor.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus for accurately calibrating an attenuation map for ECT are described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention.

Figure 1:
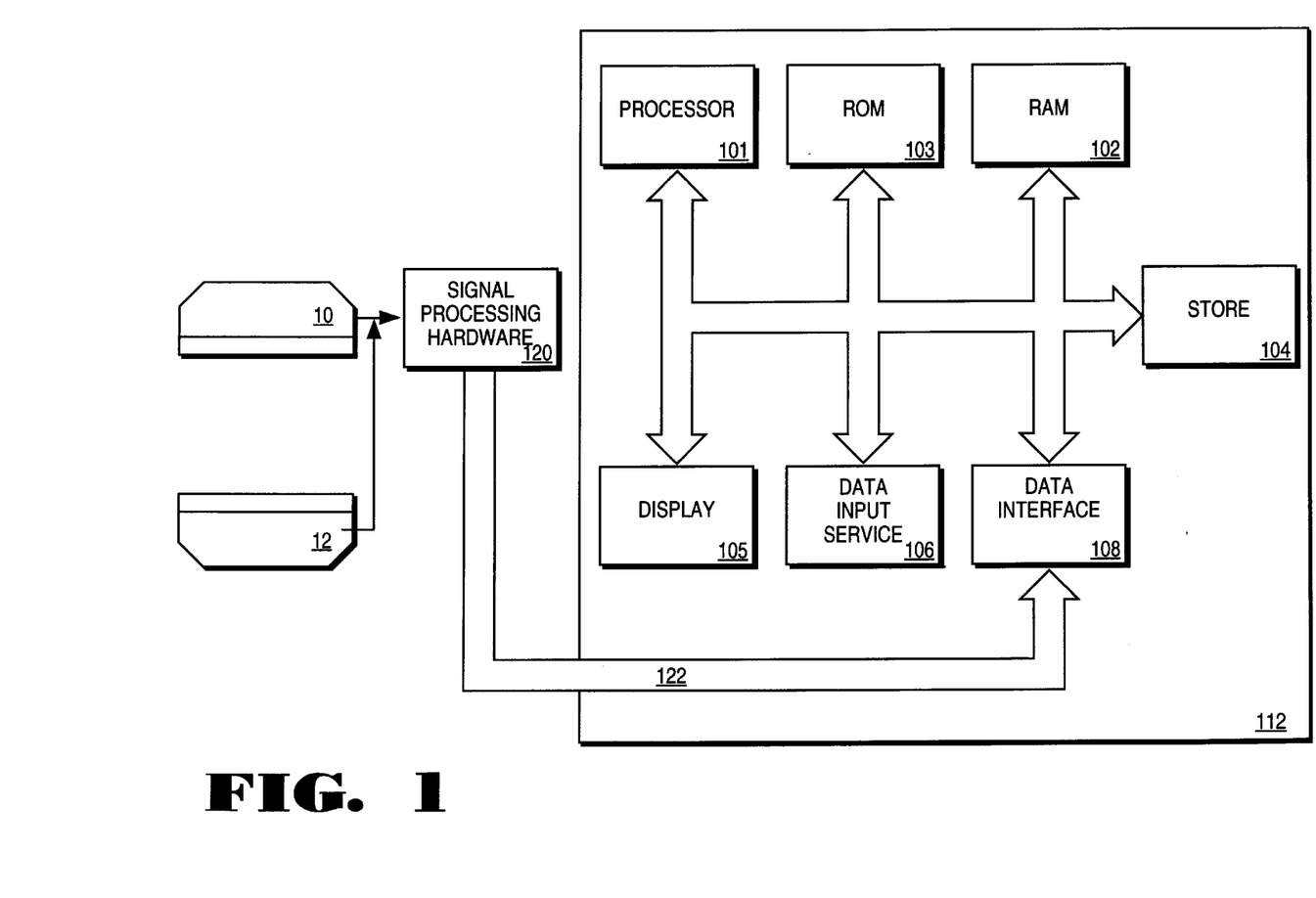
FIG. 1 is a block diagram of a gamma camera system.

FIG. 1 illustrates a gamma camera system which may be used in accordance with the present invention. The gamma camera system includes a general purpose computer system 112 used by the present invention for processing image information supplied from scintillation detectors 10 and 12. The general purpose computer system 112 is capable of processing of emission and transmission projection and image data. The computer system 112 also controls movement of detectors 10 and 12 on a gantry and controls motion controllers for controlling the movement of transmission line sources, which are discussed below.

The computer system 112 includes an address/data bus 100 for communicating information within the system; a central processing unit (CPU) 101 coupled to the bus 100 for executing instructions and processing information; a random access memory (RAM) 102 coupled to the bus 100 for storing information and instructions for the central processor 101; a read only memory (ROM) 103 coupled to the bus 100 for storing static information and instructions for the processor 101; a mass storage device 104 coupled to the bus 100 for storing image information and instructions; a display device 105, such as a cathode ray tube (CRT), coupled to the bus 100 for displaying information to computer user; an alphanumeric input device 106 including alphanumeric and function keys coupled to the bus 100 for communicating information and command selections to the central processor 101; a cursor control device (part of the data input device 106) coupled to the bus for communicating user input information and command selections to the central processor 101; and, a data interface device 108 coupled to the bus 100 for communicating command selections to the processor 101. A hard copy device, such as a printer, may also be coupled to bus 100. The display device 105 of FIG. 1 utilized with the computer system 112 of the present invention may be a liquid crystal device (LCD), cathode ray tube (CRT), or other display device suitable for creating graphic images and alphanumeric characters recognizable to the user. The mass storage device 104 may be a magnetic or optical disk and disk drive or other similar device.

The computer system 112 interfaces with scintillation detectors 10 and 12 via signal processing hardware circuits 120 over bus 122. The signal processing hardware 120 comprises amplification circuitry and analog-to-digital conversion circuits for converting channel signals from the detectors to digital data for transmission to the computer system 112. In particular, signal processing hardware 120 converts the outputs of photontultiplier tubes in detectors 10 and 12 into spatial coordinate data and energy data for detected scintillation events.

Transmission and emission data are stored in memory 102 in matrix form. Separate matrices may be used to store transmission and emission data, respectively. Non-uniform attenuation maps derived from transmission scanning are also stored in memory 102 in matrix form as part of processing. Each cell, or "bin", of a matrix corresponds to one pixel in an output image. Once image matrices are collected at different ECT angles, tomographic reconstruction is performed to generate multiple slice images, i.e., a three-dimensional image of an organ.

Figure 2:
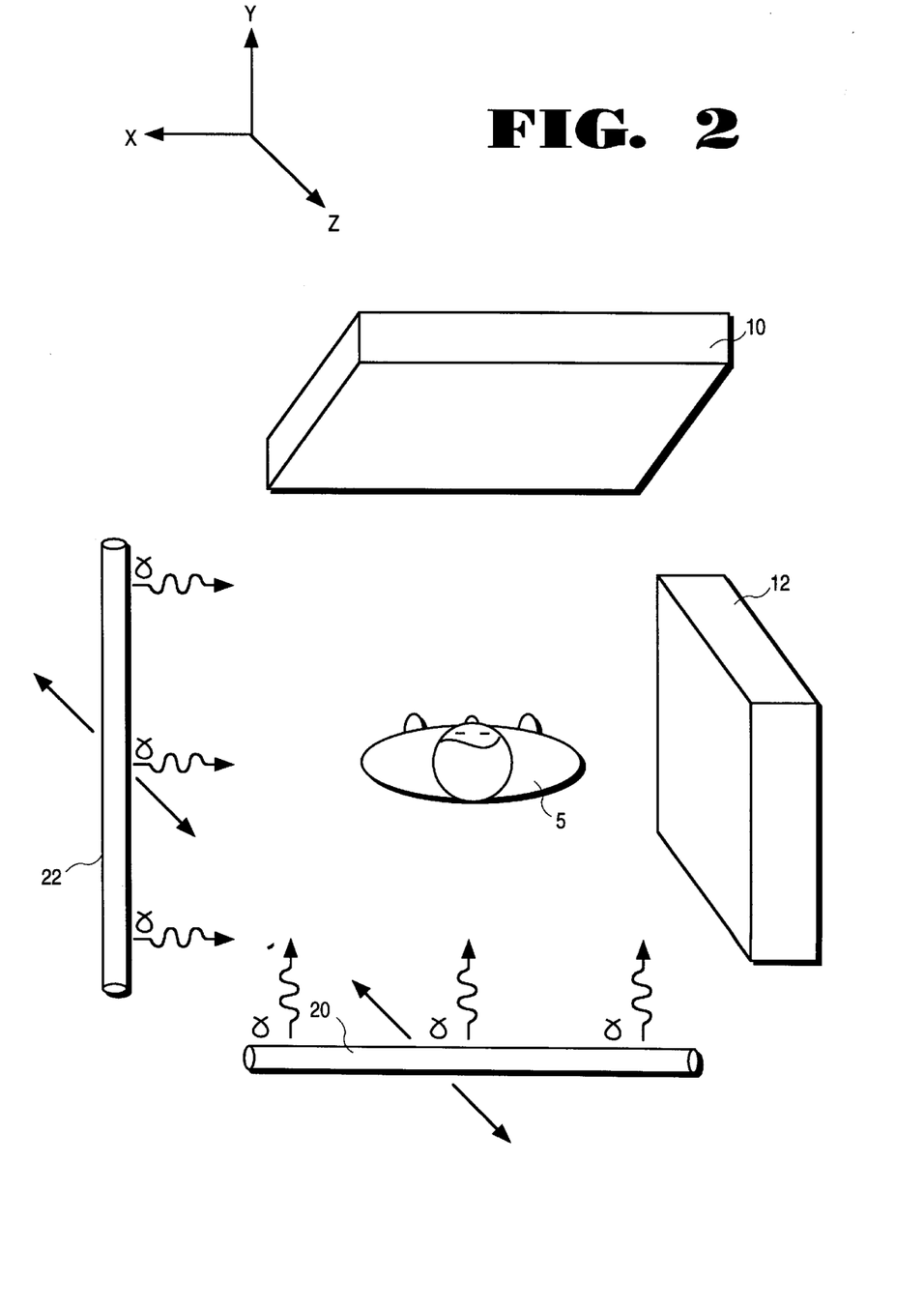
FIG. 2 illustrates portions of a gamma camera system configured for performing a transmission scan of a patient.

FIG. 2 shows portions of a gamma camera system configured to perform a transmission scan of a patient 5. Data acquired using the transmission scan may be used to generate an attenuation map for correcting emission data. In performing the transmission scan, scintillation detectors 10 and 12 are positioned in a 90° orientation, as shown in FIG. 2. Transmission line sources 20 and 22 are used to transmit gamma radiation through the patient 5 to detectors 10 and 12, respectively. For various different angles about the Z axis, line sources 20 and 22 are translated across the fields-of-view of detectors 10 and 12, respectively. Detectors 10 and 12 measure the amount of radiation from line sources 20 and 22, respectively, which passes completely through the patient 5. Using this configuration, transmission scanning may be performed simultaneously with emission scanning, provided different energy levels are assigned for the emission and transmission scans.

In general, attenuation of photons within an absorber can be described by the following equation:

$$I = I_O e^{-\mu X} \quad (1)$$

where:

I represents the intensity of the photon beam transmitted through a thickness x of the absorber;

$I_o$ represents the intensity recorded with no absorber present;

$\mu$ represents the linear attenuation coefficient of the absorber at the photon energy level of interest; and x represents the thickness of the absorber through which the photons pass.

Figure 3:
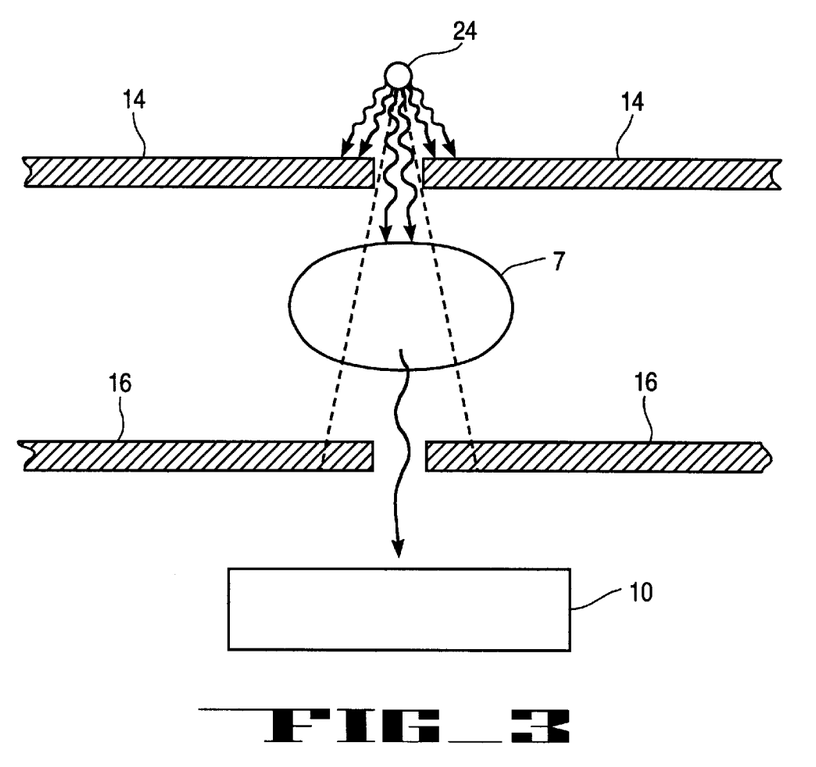
FIG. 3 illustrates conceptually a narrow-beam geometry for measurement of photon attenuation.

Equation (1) generally holds true for a "narrow-beam geometry," an example of which is illustrated conceptually in FIG. 3. In a narrow-beam geometry, photons from a source 24 are collimated using a narrow-aperture source collimator 14. The photons pass through an absorber 7 and then through a detector collimator 16 before reaching a detector 10.

Figure 4:
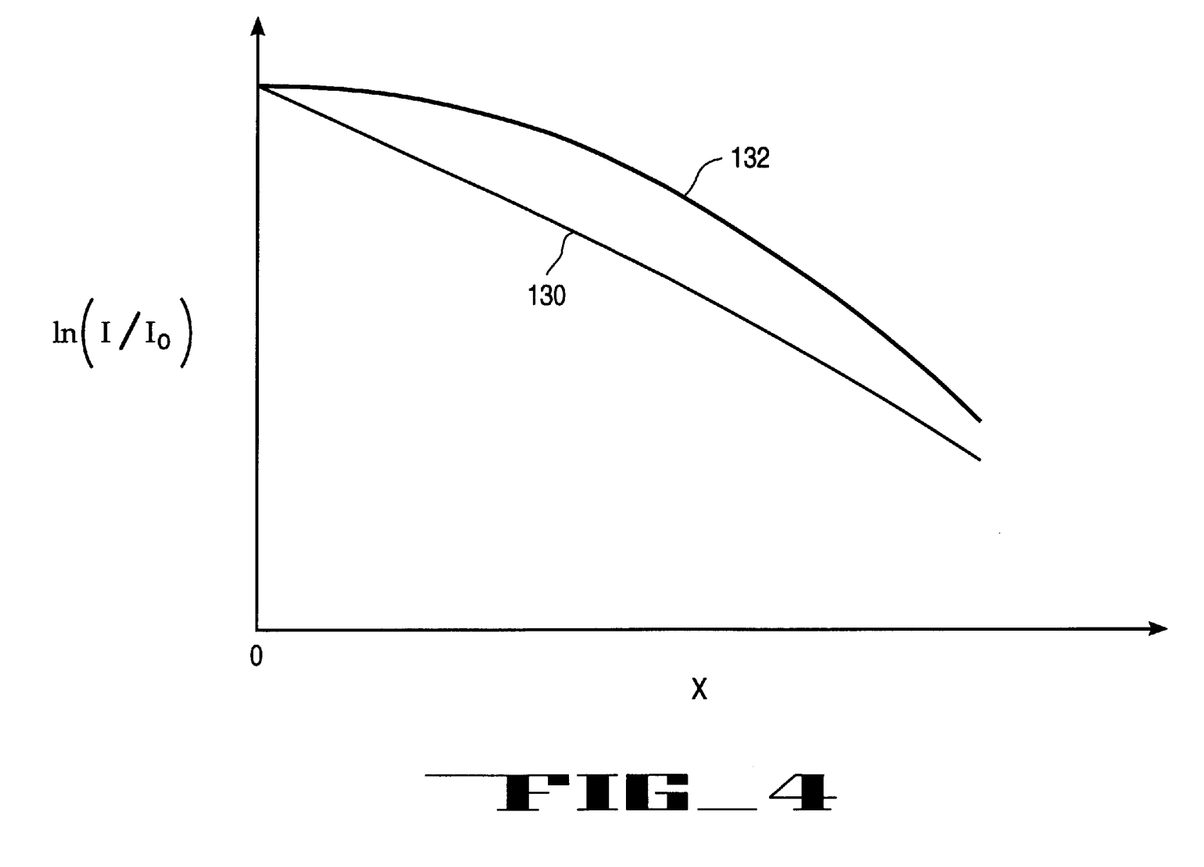
FIG. 4 is a graph showing a comparison of photon attenuation in narrow-beam and broad-beam geometries.

The value of the linear attenuation coefficient $\mu$ for an absorber can be obtained from a plot of $\ln(I/I_o)$ vs. x. Referring now to FIG. 4, the resulting plot for a true narrow-beam geometry, is a line 130, such that the magnitude of the line's slope equals the attenuation coefficient $\mu$. In practice, however, the actual geometry involved when imaging a patient is not a true narrow beam geometry. In the absence of a narrow-beam geometry, there is significant scattering within the body of photons emitted by an organ of interest during emission imaging. As a result of such scattering and other factors, the plot of $\ln(I/I_o)$ vs. x in such a geometry is not linear and more closely resembles curve 132 of FIG. 4. This lack of linearity reflects the fact that the actual attenuation coefficient $\mu$ in such a case is not constant for the absorber (i.e., for the body). Rather, the attenuation coefficient, varies as a function of x. Consequently, the use of an accepted, "textbook" value of the attenuation coefficient $\mu$ for purposes of calibrating an attenuation map may cause artifacts in the final output images because of variations in the actual value of $\mu$ as will now be explained.

As noted above, transmission scanning and emission scanning are generally performed simultaneously by assigning a different energy level for the transmission scan than for the emission scan. Because the attenuation map is generated from the transmission scan, the attenuation map initially corresponds to the energy level used for the transmission scan. Consequently, the attbuation map must be scaled to the energy level used for the emission scan in order to use the map to correct emission data. As noted above, the attenuation map comprises a matrix of values. To scale the attenuation map to the emission level, the values in the matrix generally are multiplied by a scale factor K. In performing the scaling operation, the processor 101 of the gamma camera system executes computer program instructions that define the scaling operation. The value of the scaling factor K may be included in these instructions prior to execution of the code, or the value (or any component thereof) may be read in as a data value during execution.

One possible approach to determining the scaling factor K is to first identify a substance that has a composition similar to that of the object of interest (i.e., the patient), and to then base the scaling factor upon "textbook" values of the attenuation coefficient $\mu$ for that substance. For example, because the human body is composed mostly of water, the attenuation coefficient of water $\mu_{H_2O}$ may be used as an approximation of the attenuation coefficient of the human body. Therefore, the scaling factor K might be taken to be the ratio of the attenuation coefficient of water $\mu_{H_2O}$ at the emission energy level to the attenuation coefficient of water $\mu_{H_2O}$ at the transmission energy level, as shown in equation (2).

$$K = \frac{\mu_{H_2O, \text{Emission Energy}}}{\mu_{H_2O, \text{Transmission Energy}}} \quad (2)$$

Textbook values of $\mu_{H_2O}$ for use in equation (2) are available for different energy levels from numerous well-known sources. Although the scaling factor K of equation (2) might seem to be a logical choice, in actual practice such a scaling factor tends to produce disappointing results. In particular, because of scattering of photons within the human body and the distribution of photons over a range of energy levels, such a scaling factor proves to be inaccurate, causing image artifacts to be generated. Therefore, in accordance with the present invention, this problem is solved by first determining an effective attenuation coefficient for water $\mu_{EFF,H_2O}$ for an emission energy level, and then using the effective attenuation coefficient, rather than textbook values attenuation coefficient, in the scaling factor used to scale the attenuation map. Hence, a scaling factor K' is used according to the present invention and is computed according to equation (3).

$$K' = \frac{\mu_{EFF, H_2O, \text{Emission Energy}}}{\mu_{H_2O, \text{Transmission Energy}}} \quad (3)$$

For purposes of illustration, assume an energy level of 72 keV is selected for emission scanning using Tl-201 (Thallium), whereas an energy level of 100 keV is selected for transmission scanning using Gd-153 (Gadolinium) sources. It should be appreciated, however, that the present invention is not limited to any specific energy levels. According to the present invention, an effective attenuation coefficient $\mu_{EFF,H_2O}$ is determined for water for the emission energy level. Later, during an imaging session, an attenuation map is generated using a transmission scan at the transmission energy level. The attenuation map is then scaled to the emission energy level by multiplying the coefficient values of the attenuation map by the scaling factor K' of equation (3).

Figure 6:
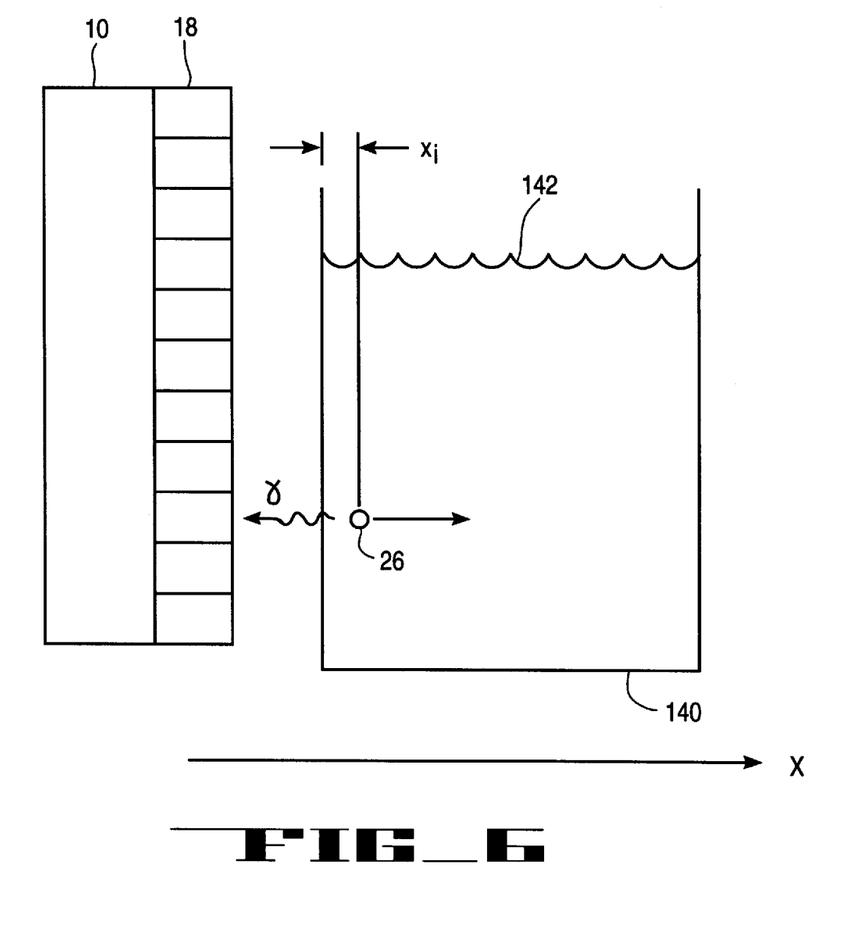
FIG. 6 illustrates a test set-up for measuring an effective attenuation coefficient for water.

In accordance with the present invention, the effective attenuation coefficient $\mu_{EFFH_2O}$ is determined empirically by using the test configuration of FIG. 6 to acquire radiation count data. Referring to FIG. 6, a container 140 is filled with water 142. A scintillation detector 10 with a collimator 18 is placed next to the container 140. First, the intensity Io of photons emitted from a radiation source 26 is measured in terms of counts by placing the source 26 next to the detector 10 (step 501). The source 26 is selected to be the same radionucleides used in the patient study.

Therefore, given the illustrative energy levels assumed above, the source 26 would be selected to have an energy level of 72 keV, which is the desired emission energy level. Next, a container 140 is placed next to the detector 10, and the source 26 is submerged in the water 142. It is preferable that the size and positioning of the container 140 relative to the detector 10 be sufficiently large, such that the container 140 effectively overlaps completely the field of view of the detector 10. The intensity $I_i$ of photons passing through the water 142 is then measured in terms of counts for a number of different values of x (i.e., $x_i$), as shown in FIG. 6, (step 502). The intensity is determined by summing all of the counts in a constant sized region of interest which is larger than the image of the object at all depths, $x_i$.

It is preferable that four or more values of $x_i$ be used to measure $I_i$.

Further, the range of values of $x_i$ need only reflect the range of distances which photons are likely to travel within the human body; therefore, a range of $x_i$ of 0 to approximately 20 centimeters with an increment of 5 centimeters or less between values of $x_i$ should be sufficient.

Figure 5:
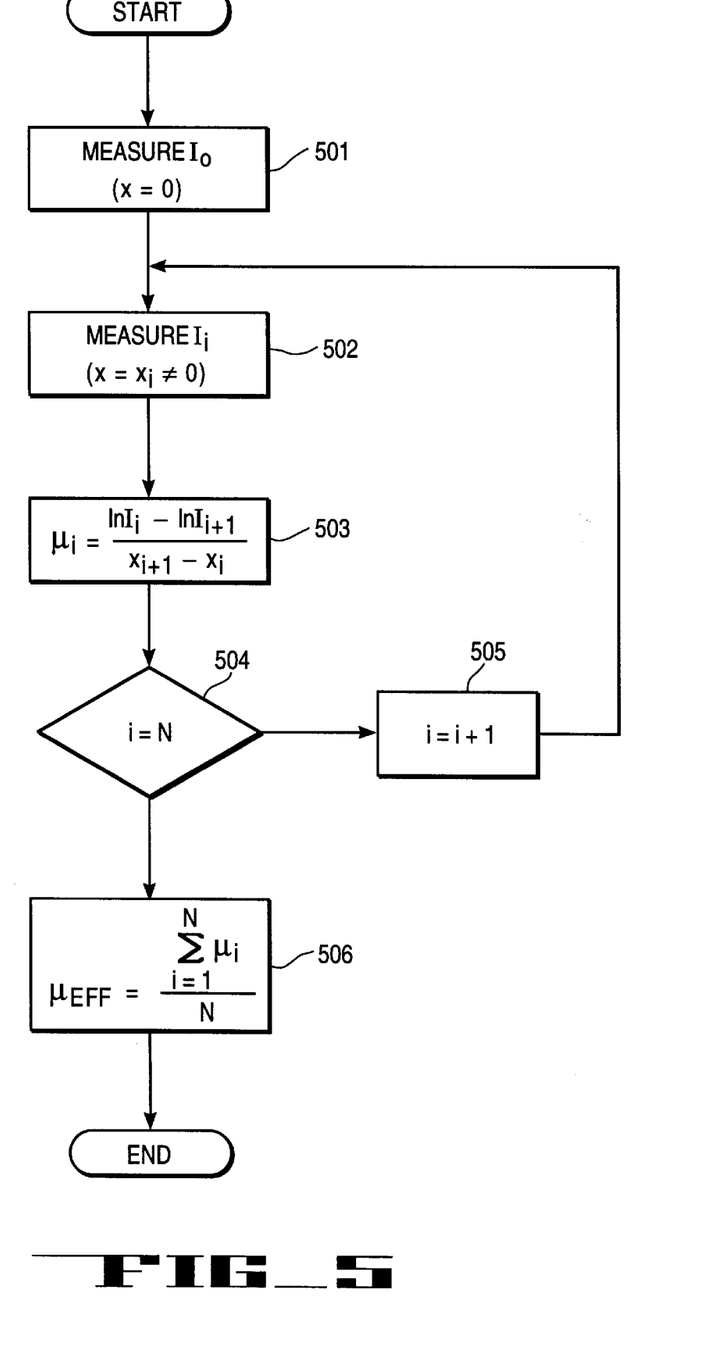
FIG. 5 is a flow diagram illustrating a routine for empirically determining an attenuation coefficient.

Various methods may be used to determine the value of the effective attenuation coefficient $\mu_{EFF,H_2O}$ from the acquired count data. FIG. 5 illustrates one such method. In the routine FIG. 5, the value of $\mu_{EFF,H_2O}$ is determined according to equation (4) (step 506), where $\mu i$ is defined by equation (5) (step 503).

$$\mu_{EFF,H_2O} = \frac{\sum_{i=1}^{N} \mu_i}{N} \quad (4)$$

where:

$$\mu_i = \frac{\ln I_i - \ln I_{i+1}}{x_{i+1} - x_i} \quad (5)$$

Note that, at x =0, the radiation source is placed against the wall of the container 140. In the preferred embodiment, the container 140 is chosen to have a sufficiently small thickness, such that the container 140 causes no appreciable attenuation.

Figure 7:
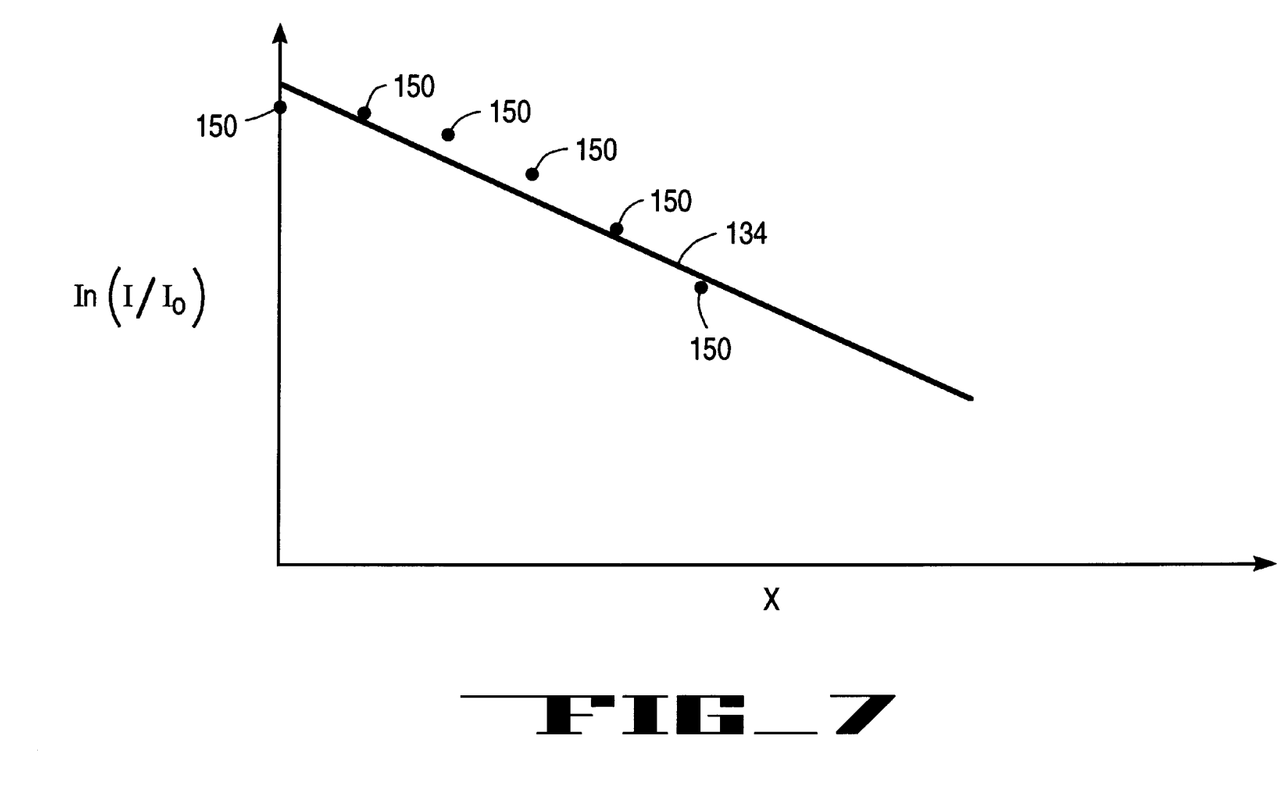
FIG. 7 is a graph of sample data obtained in measuring an effective attenuation coefficient for water.

Another method of determining $\mu_{EFF,H_2O}$ using the test setup of FIG. 6 is to determine a best-fit line of data points representing $\ln(I/I_o)$ for various values of x. The magnitude of the slope of the best fit line will then represent the value of the effective attenuation coefficient $\mu_{EFF,H_2O}$ of water at the emission energy level. FIG. 7 shows a sample plot of $\ln(I/I_o)$ for various values of x acquired using the test setup of FIG. 6. A best-fit line 134 for the data points 150 may be visually plotted or determined by use of a well-known linear regression formula.

Thus, in accordance with the present invention, the scaling factor K' of equation (3), which incorporates an effective attenuation coefficient $\mu_{EFF,H_2O}$ is used to scale an attenuation map to an emission energy level, rather than the scaling factor K of equation (2), which makes use of textbook values of $\mu_{H_2O}$. As a result, the final output images obtained are of higher quality, since the scaling factor is more accurate.

In general, a radiopharmaceutical used in emission imaging produces gamma rays which are concentrated in one or more narrow energy ranges, each centered about a peak energy level, or "photo peak." Accurate scaling of an attenuation map can be complicated by the use of a radiopharmaceutical having more than one photopeak, such as Tl-201, which has photopeaks at 72 keV and 167 keV. The fact that the radiated energy may be largely concentrated at one particular photopeak for a given radiopharmaceutical should be taken into consideration when scaling the attenuation map. Therefore, a variation of the above-described technique may be used in situations in which a multiple-photopeak radionuclide is used for emission studies, as will now be described.

When a multiple-photopeak radiopharmaceutical is to be used, the empirical method described above is used to determine an effective attenuation coefficient for each photopeak. For a radiopharmaceutical having N photopeaks used for emission imaging, the overall effective attenuation coefficient, $\mu_{EFF,H_2O}$ is then computed as the sum of the effective attenuation coefficients for each photopeak, $\mu_{EFF, peak-i}$ weighted appropriately based on the abundance (percent count distribution), $A_{peak-i}$, at each photopeak, as shown in equation (6).

$$\mu_{EFF,H_2O} = \sum_{i=1}^{N} (\mu_{EFF,Peak\_i})(A_{peak\_i}) \quad (6)$$

Figure 8:
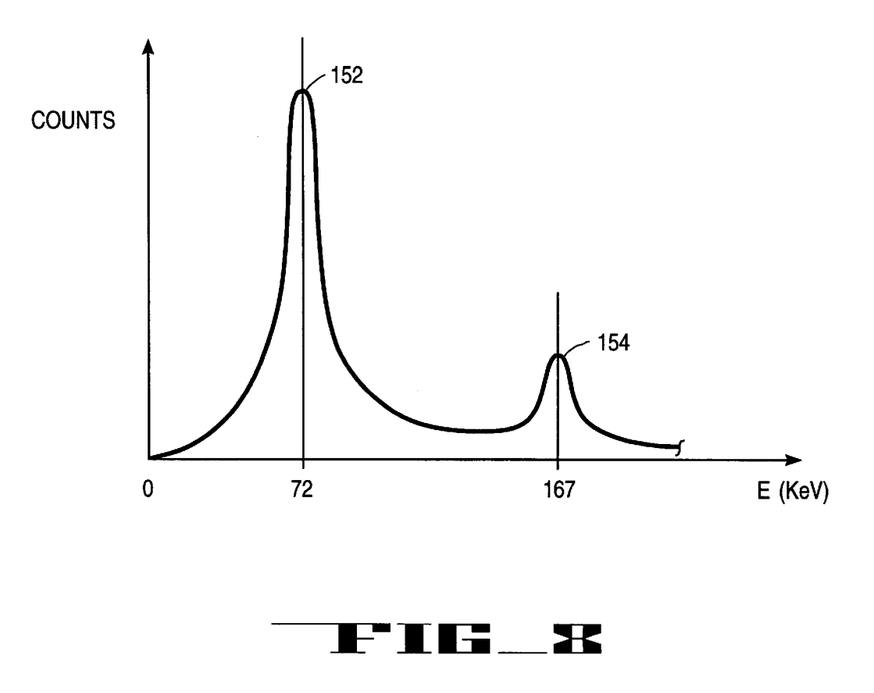
FIG. 8 illustrates the energy distribution for a radiopharmaceutical having multiple photopeaks.

This technique is now illustrated with reference to FIGS. 8 and 9. FIG. 8 illustrates an approximation of the energy spectrum of Tl.

Approximately 90 percent of the radiated emissions for Tl is concentrated around 72 keV, while approximately 10 percent of the radiated energy for Tl is concentrated around 167 keV. Hence, the method described above in connection with FIGS. 5 through 7 is used to obtain two sets of data representing $\ln(I/I_o)$ vs. x, as shown in FIG. 9. Accordingly, two best-fit lines 156 and 158 are generated for photopeaks 152 and 154, respectively. The slope of line 158 represents the effective attenuation coefficient $\mu_{EFF,72}$ for the 72 keV photopeak, while the slope of line 156 represents the effective attenuation coefficient $\mu_{EFF,167}$ for the 167 keV photopeak. Therefore, the overall effective attenuation coefficient $\mu_{EFF,H_2O}$ in this case is computed according to equation (7).

$$\mu_{EFF,H_2O}=0.9(\mu_{EFF,72})+0.1(\mu_{EFF,167}) \quad (7)$$

An alternative to this method of handling multiple photopeaks is to calibrate the attenuation map separately for each photopeak, using the above-described empirical method and then sum the corrected data.

Figure 9:
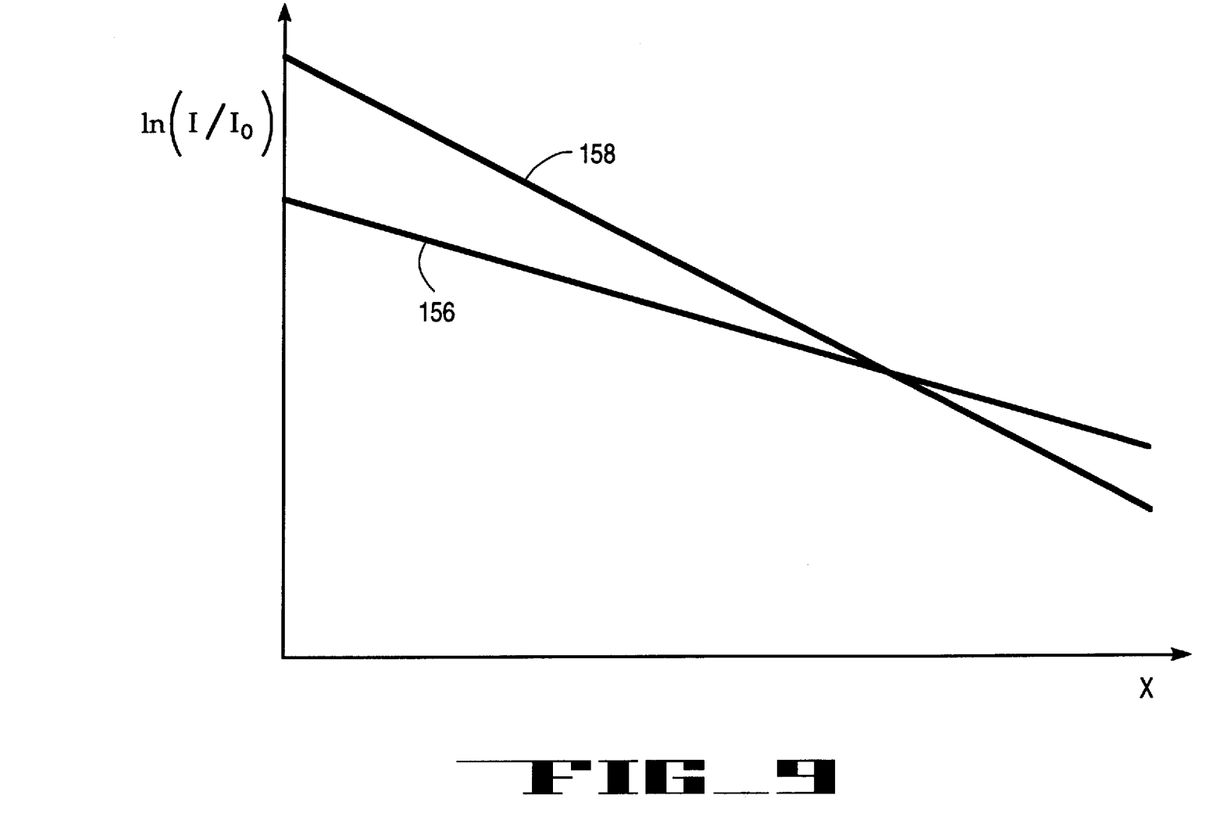
FIG. 9 is a graph of sample data for a radiopharmaceutical having multiple photopeaks.
Figure 10:
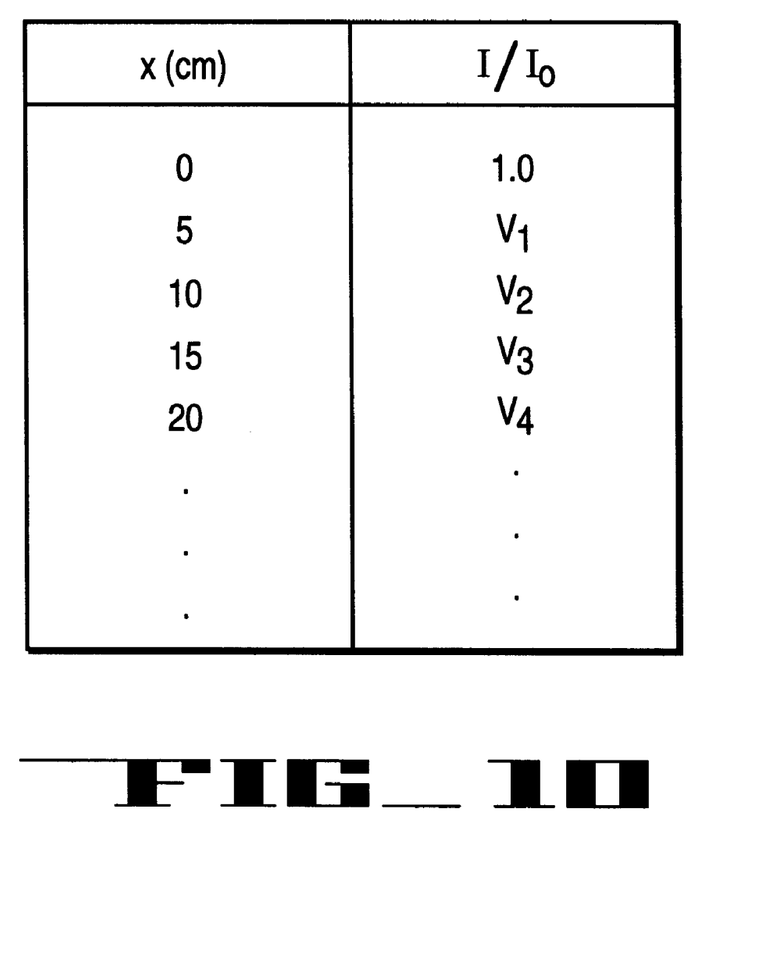
FIG. 10 illustrates a look-up table storing attenuation values for various values of path length.

Referring now to FIGS. 8 through 10, a technique is now described for correcting emission data for the effects of attenuation, which does not require calibration of an attenuation map. In particular, the data values 150 illustrated in FIG. 7 are stored in a look-up table within the computer system 112 before imaging is performed. FIG. 10 illustrates an example of one such look-up table. The look-up table contains experimentally-determined attenuation values of $I/I_o$ in one column for various values of path length x in another column, as shown in FIG. 10. The attenuation values in the look-up table are then used to approximate the actual attenuation of photons on a pixel-by-pixel basis for each projection angle during reconstruction of the emission image.

In the preferred embodiment, the look-up table is stored in RAM 102 and read by the processor 101 during calibration of the attenuation map. The look-up table may be initially provided to the imaging system via mass storage device 104, or it may be stored in ROM 103.

Figure 11:
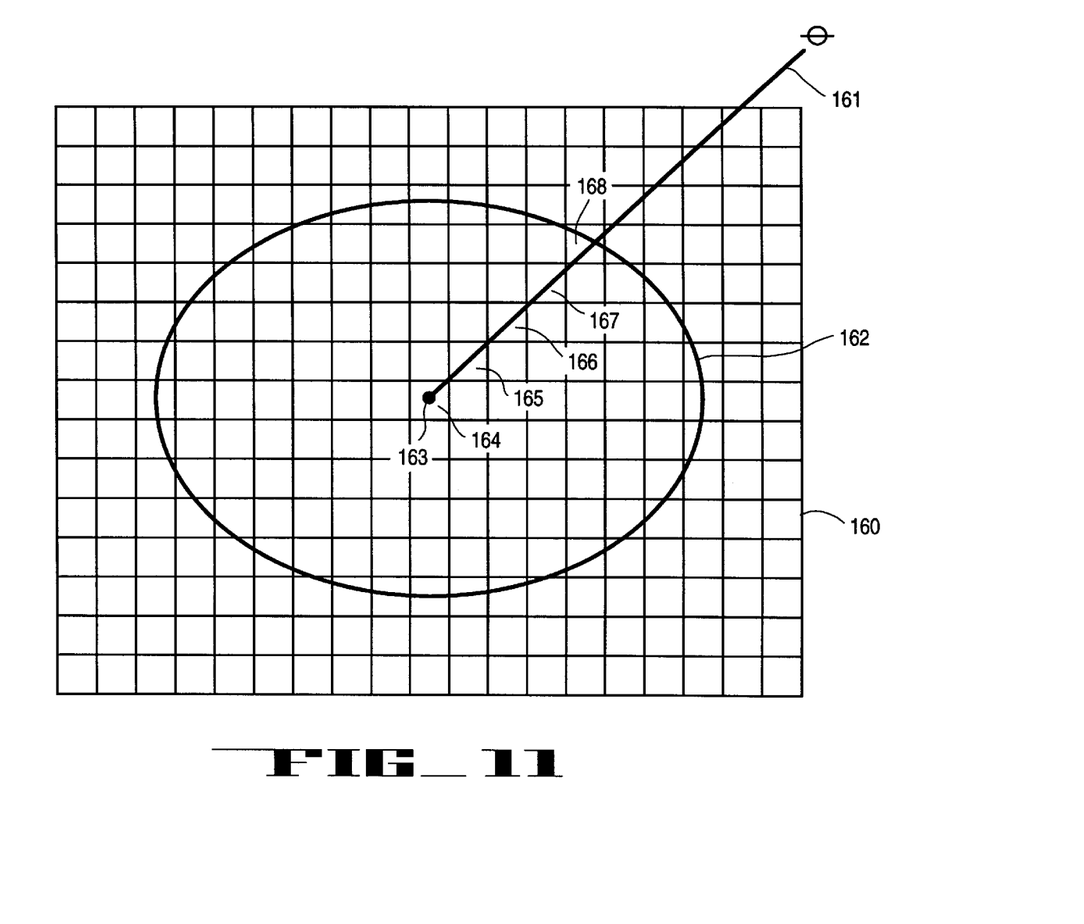
FIG. 11 illustrates an emission image matrix.
Figure 12:
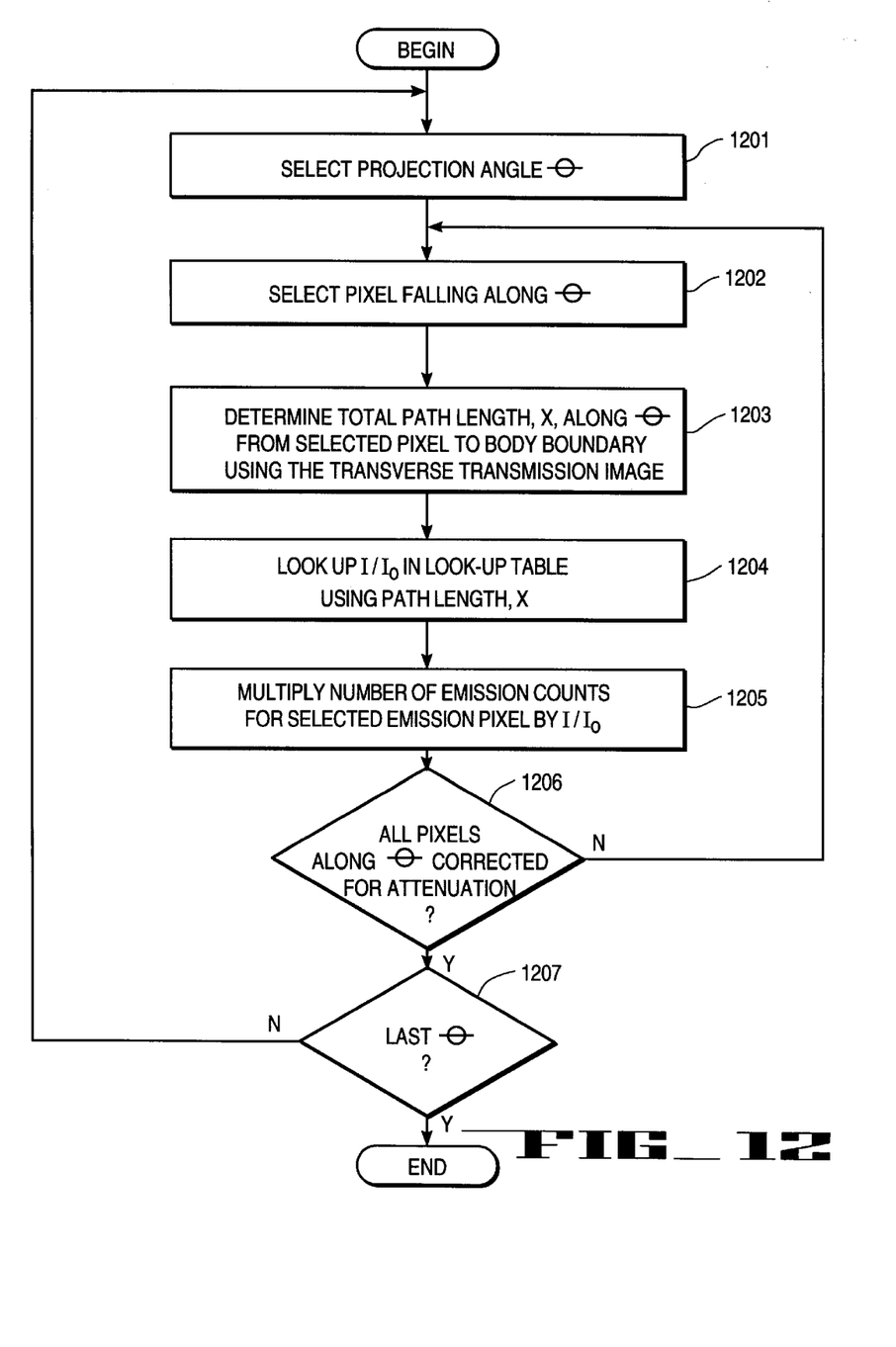
FIG. 12 is a flow diagram illustrating a routine for performing attenuation correction of emission ECT data.

The technique of performing attenuation correction is now described with respect to FIGS. 10 through 12. FIG. 11 illustrates a representative matrix 160 of emission image data corresponding to one transverse (x-y) slice of an emission scan. The matrix 160 includes a number of pixels. Referring to FIGS. 11 and 12, the method of performing attenuation correction begins with the selection of a projection angle θ (step 1201). Next, a pixel is selected which falls along the projection angle θ (step 1202). In other words, a pixel is selected which is intersected by a line 161 passing through the center point 163 in the matrix 160 (representing the center of rotation of the detectors) at the current projection angle θ. Thus, in FIG. 11, pixel 164 is initially selected. Next, the total path length x from the selected pixel to the body boundary 1662 along the line 161 is computed (step 1203). This path length x represents the distance traveled through the body along θ by a photon originating from the position represented by the selected pixel. Note that methods of locating the body boundary in tomographic data are well-known. For example, the path length x can be determined from the corresponding pixel in the transverse transmission image. For the computed path length x, the corresponding value for the ratio $I/I_o$ is then determined from the look-up table (step 1204).

Note that the actual values of path length x computed during this procedure may not coincide exactly with the values of x stored in the look-up table. Therefore, interpolation or any other appropriate method can be used to derive a value of the $I/I_o$ ratio for a value of path length x that is not explicitly listed in the look-up table. Alternatively, the stored value of path length x which is closest to the computed value (step 1203) can be used as an approximation.

Once the value of the $I/I_o$ ratio is determined from the look-up table, this value is applied to the emission pixel value of the selected pixel (step 1205). That is, the number of counts of the selected pixel is multiplied by the ratio $I/I_o$ to produce a pixel value that is corrected for attenuation. If there are pixels in the matrix 160 along θ (i.e., pixels intersected by line 161) which have not yet been corrected (step 1206), then the above routine is repeated for each additional pixel along θ out to the body boundary 162 (e.g., pixels 165–168 in FIG. 11). This process is then repeated for each additional projection angle θ (step 1207). The resulting matrix after completion of the above routine has been corrected for attenuation.

Thus, a method and apparatus for accurately calibrating an attenuation map and performing attenuation correction for ECT have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of enabling a medical imaging system to perform attenuation correction of emission data of an object, the emission data acquired during an imaging session and including a plurality of pixels representing locations within the object, the imaging system including a processor, the method comprising the steps of:

performing measurements prior to the imaging session to determine a plurality of attenuation values using an attenuation medium other than the object but representative of the object, each of the attenuation values corresponding to one of a plurality of thicknesses of the attenuation medium;

storing the attenuation values and a plurality of corresponding thickness values prior to the imaging session in a storage medium accessible to the processor, the stored attenuation values for use by the processor in correcting the emission data of the object; and for each of the plurality of pixels, and for each of a plurality of projection angles for each pixel, using the processor to determine the length of a path from a point within the object represented by the pixel to a boundary of the object along the projection angle;

select one of the plurality of stored thickness values based on the determined length;

identify one of the plurality of stored attenuation values corresponding to the selected thickness value; and adjust a value of the pixel based on the identified attenuation value.

2. A method according to claim 1, wherein the step of storing the attenuation values and a plurality of corresponding thickness values comprises the step of storing the attenuation values and the corresponding thickness values in a look-up table.

3. A method according to claim 1, wherein the step of performing measurements prior to the imaging session comprises, for each of a plurality of values of thickness of the attenuating medium, the steps of:

transmitting photons from a transmission source through said thickness of the attenuating medium;

counting the number of photons transmitted by the transmission source that pass completely through said thickness of the attenuating medium; and determining one of the attenuation values based on the counting step.

4. A method according to claim 1, wherein the attenuating medium is water.

5. In a gamma camera system, a method of correcting emission images of an object for effects of attenuation, the method comprising the steps of:

detecting emission radiation emitted from the object from a plurality of angles;

reconstructing the emission projection data to generate emission image data, the emission image data including a plurality of pixels representing locations within the object, wherein a path length is associated with each pixel for each of the angles, each path length representing a distance from a point within the object represented by said pixel to a boundary of the object; and for each pixel:

selecting a length value of a plurality of stored length values wherein the selected length value is based on the path length for said pixel for a given angle;

based on the selected length value, accessing an attenuation value of a plurality of stored attenuation values, each of the plurality of stored attenuation values corresponding to one of the plurality of stored length values; and adjusting the pixel based on the accessed attenuation value.

6. A method according to claim 5, wherein each of the plurality of stored length values represents a different thickness of a model attenuation medium representative of the object, and wherein each of the plurality of stored attenuation values is an attenuation value of the model attenuation medium, the model attenuation medium having a linear attenuation coefficient substantially similar to a linear attenuation coefficient of the object, each of the plurality of stored attenuation vales having been generated experimentally prior to the imaging session.

7. A method according to claim 6, wherein the attenuation value is derived based on the steps of:

transmitting photons from a transmission source through the given thickness of the model attenuation medium;

counting the number of photons transmitted by the transmission source that pass completely through said thickness of the model attenuation medium; and determining the attenuation value based on the counting step.

8. A method according to claim 7, wherein the model attenuation medium is water.

9. A medical imaging system for generating images of a object, comprising:

a detector for detecting emission radiation emitted from the object, the emission radiation being subject to attenuation within the object;

a processor coupled to the detector;

a storage device coupled to the processor, the storage device having stored therein a plurality of attenuation values and a plurality of corresponding thickness values, each of the attenuation values representing a measure of the attenuation by one of a plurality of thicknesses of an attenuation medium other than the object but representative of the object, and each of the stored thickness values corresponding to one of said thicknesses of the attenuation medium; and wherein the processor is configured to:

control the detector to acquire emission data of the object based on the emission radiation, the emission data including a plurality of pixels representing locations within the object;

correct the emission data for attenuation by, for each pixel, and for each of a plurality of projection angles for each pixel determining the length of a path from a point within the object represented by the pixel to a boundary of the object along the projection angle;

selecting one of the plurality of stored thickness values based on the determined length;

identifying one of the plurality of stored attenuation values corresponding to the selected thickness value; and adjusting a value of the pixel based on the identified attenuation value.

10. A medical imaging system according to claim 9, wherein the attenuation medium is water.

11. A medical imaging system according to claim 9, wherein the attenuation values and the thickness values are stored in a look-up table.

12. A program storage device readable by a machine, the storage device tangibly embodying a program of instructions executable by a processor in a medical imaging system to perform steps for enabling the medical imaging system to correct emission data of an object being imaged for effects of attenuation in the object, the emission data including a plurality of pixels representing locations within the object, the steps comprising:

detecting emission radiation emitted from the object to acquire emission data;

maintaining, in a look-up table in a storage device, a plurality of stored attenuation values, each of the attenuation values representing a measure of attenuation caused by a corresponding thickness of an attenuating medium other than the object but representative of the object, the look up table further having stored therein a plurality of thickness values representing a plurality of thicknesses of the attenuation medium; and     correcting the emission data of the object based on the attenuation values by, for each of the plurality of pixels, and for each of a plurality of projection angles for each pixel         determining the length of a path from a point within the object represented by the pixel to a boundary of the object along the projection angle;

selecting one of the plurality of stored thickness values based on the determined length;

identifying one of the plurality of stored attenuation values corresponding to the selected thickness value; and         adjusting a value of the pixel based on the identified attenuation value.

13. A program storage device according to claim 12, wherein the attenuation values have been determined prior to an imaging session by performing the steps of:

for a plurality of thicknesses of the attenuating medium, transmitting radiation from a transmission source through each said thickness;

for each said thickness, detecting the amount of radiation transmitted by the transmission source which passes through said thickness; and     calculating an attenuation value based on the detected amount of radiation transmitted by the transmission source which passes through said thickness.

14. A program storage device according to claim 12, wherein the attenuating medium is water.

15. A program storage device according to claim 12, further comprising the step of computing the attenuation values based on a plurality of experimentally-determined attenuation measurements.

16. A method of correcting emission image data of an object for attenuation, the emission image data including a plurality of pixels representing locations within the object, the method comprising, for each pixel, and for each of a plurality of projection angles for each pixel:

determining the length of a path from a point within the object represented by the pixel to a boundary of the object along the projection angle;

identifying an attenuation value corresponding to the determined length of the path, from a plurality of stored attenuation values; and     adjusting a value of the pixel based on the identified attenuation value.

17. A method according to claims 16, wherein each of the plurality of stored attenuation values is an attenuation value of the model attenuation medium, and wherein each of the plurality of stored attenuation vales corresponds to a different thickness of the model attenuation medium and has been generated experimentally prior to an imaging session during which the emission data was acquired.

18. A medical imaging system comprising:

means for acquiring radiation emission data of an object during an imaging session, the emission image data including a plurality of pixels representing locations within the object;

means for determining the length of a path from a point within the object represented by a pixel to a boundary of the object along the projection angle, for each pixel and for each of a plurality of projection angles for each pixel;

means for selecting a stored length value based on the determined length, the stored length value representing a thickness of a model attenuation medium other than the object to be imaged but representative of the object to be imaged;

means for identifying a stored attenuation value corresponding to the stored length value, wherein the stored attenuation value is a previously measured attenuation value of the model attenuation medium; and     means for adjusting a value of the pixel based on the identified attenuation value.

19. A method of enabling scaling of an attenuation map of an object to be imaged by a medical imaging system from a first energy level to a second energy level, the method comprising:

determining an overall effective attenuation coefficient for an attenuation medium other than the object but representative of the object, the overall effective attenuation coefficient corresponding to a radiation source having a plurality of photopeaks, wherein said determining includes:

determining, for each of the plurality of photopeaks, an effective attenuation coefficient for the attenuation medium; and         determining the overall effective attenuation coefficient as a weighted sum of the effective attenuation coefficients of the plurality of photopeaks; and     generating a scaling factor based on the overall effective attenuation coefficient, the scaling factor for use by the medical imaging system in scaling the attenuation map of the object from the first energy level to the second energy level during an imaging session.

\* \* \* \* \*